United States Patent [19]
Potts

[11] 4,167,531
[45] Sep. 11, 1979

[54] PURIFICATION OF HYDROCARBONS
[75] Inventor: Mack F. Potts, Bartlesville, Okla.
[73] Assignee: Phillips Petroleum Co., Bartlesville, Okla.
[21] Appl. No.: 824,125
[22] Filed: Aug. 12, 1977
[51] Int. Cl.² ............................................. C07C 9/00
[52] U.S. Cl. .................. 585/854; 585/723; 585/956
[58] Field of Search ................ 260/683.41, 683.48, 260/676 R

[56] References Cited
U.S. PATENT DOCUMENTS

| 2,872,936 | 2/1959 | Richardson | 137/172 |
| 3,254,137 | 5/1966 | Hutto et al. | 260/683.48 |

Primary Examiner—Delbert E. Gantz
Assistant Examiner—Joseph A. Boska

[57] ABSTRACT

In the purification of hydrocarbon streams containing HF by chemical reaction with potassium hydroxide, a small portion of the hydrocarbon stream containing HF is passed through a small test bed of solid KOH; and when excess HF is present in the hydrocarbon stream to be purified, the temperature of the test bed increases significantly and rapidly and the flow of hydrocarbon is discontinued to the main treater responsive to the temperature in the test bed thereby preventing the treater temperature from exceeding a preselected maximum allowable value. In one embodiment, the main hydrocarbon charge is by-passed around the main KOH treater and introduced into the effluent from the treater; and in another embodiment, the hydrocarbon charge is returned to a settling zone following alkylation and prior to separation facilities utilized to process the hydrocarbon phase.

7 Claims, 1 Drawing Figure

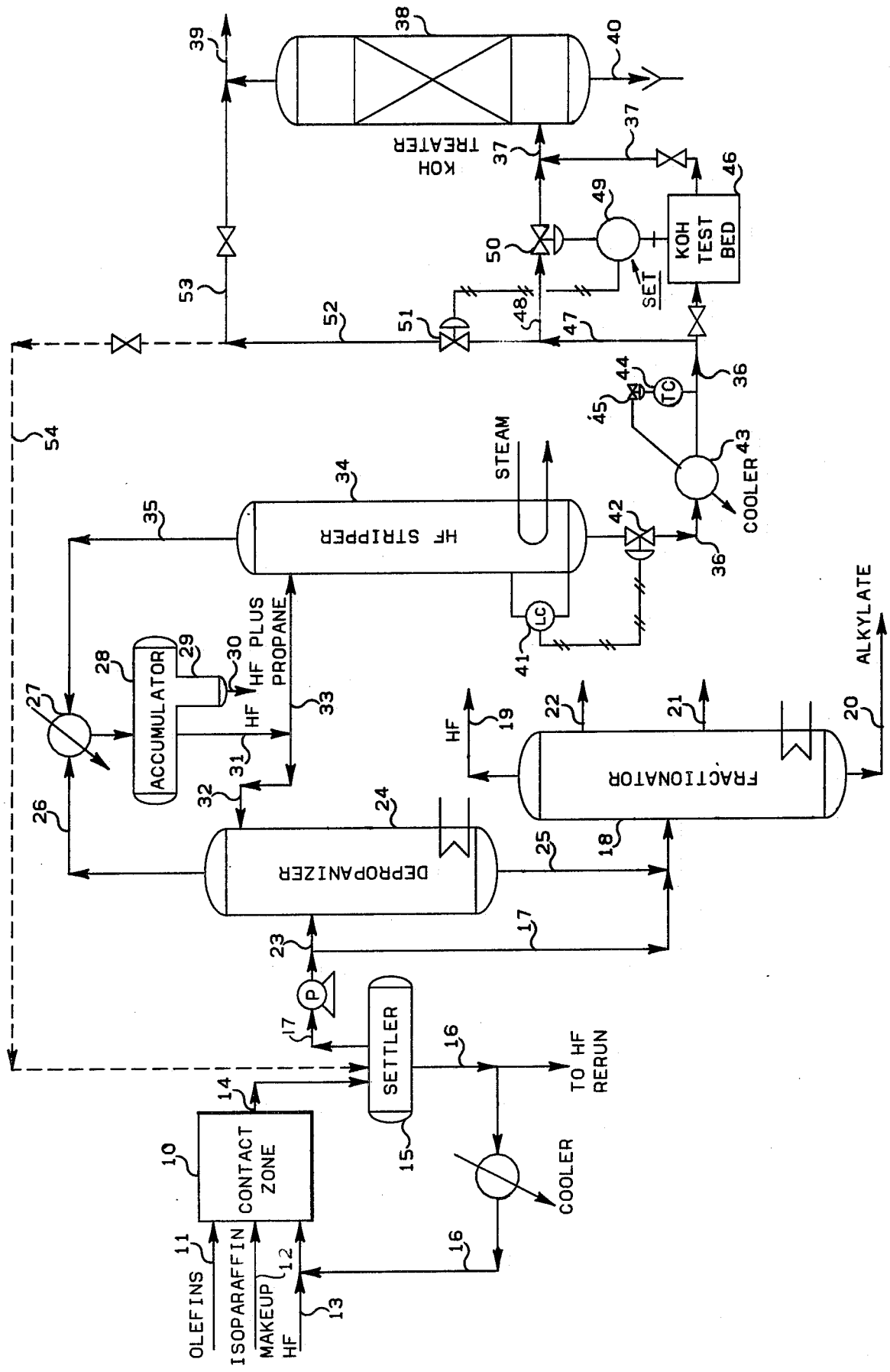

PURIFICATION OF HYDROCARBONS

This invention relates to the removal of HF from hydrocarbon streams containing same. In accordance with one aspect, this invention relates to the continuous separation of hydrofluoric acid from a hydrocarbon stream employing a solid potassium hydroxide treating agent and control of the separation whereby excessive run-away temperatures are avoided in the KOH treater. In another aspect, this invention relates to a method and apparatus for controlling purification of a hydrocarbon containing HF by contacting a portion of the hydrocarbon stream with a small test bed of solid KOH, then responsive to temperature changes in the test bed manipulating the flow of hydrocarbon to the main KOH treater wherein the flow is discontinued when excess HF is present to avoid the treater temperature from exceeding a preselected maximum allowable value.

In a process for the conversion of hydrocarbons wherein liquid hydrogen fluoride (HF) is employed as a catalyst, small amounts of HF acid and organic fluorides are present in the product streams due to the solubility of these materials in hydrocarbons. In most commercial operations, the hydrocarbon phase containing organic fluorides and HF is recontacted with relatively pure liquid HF to remove the organic fluorides therefrom, as described in U.S. Pat. No. 3,254,137, issued May 31, 1966, Hutto et al. In some operations, the propane and normal butane yields are treated with a solid reagent such as bauxite or alumina to remove organic fluorides therefrom as described in U.S. Pat. No. 3,527,840, issued Sept. 8, 1970, to Price. With substantially all of the organic fluorides removed, the propane and the normal butane separate yields can be treated with solid KOH to remove the remaining HF, as described in the above HUTTO et al patent. When organic fluorides are not first removed, as above described, then the propane and normal butane yields are each separately treated with solid KOH in the presence of added alcohol, as described in U.S. Pat. No. 3,403,198. issued Sept. 24, 1968, to Van Pool. This organic fluoride removal, using bauxite or alumina, is effected between the HF stripper and the solid lump KOH treater. KOH removes substantially only HF from the hydrocarbon.

It is necessary to remove HF from these streams before subsequent processing or blending of the hydrocarbon streams. Normally, the amount of HF present in the hydrocarbon stream is relatively small but the HF still has to be removed from the hydrocarbon streams in order that the hydrocarbons will pass the fluoride specification for the respective streams. Residual amounts of HF are ordinarily removed by contact with solid KOH. Upsets often occur in the processing equipment thereby causing excess HF in the stream to be charged to the solid bed of KOH particles. When too much HF contacts the KOH, the temperature starts to rise in the bed area due to the heat of reaction between KOH and HF. If excess HF is allowed to continue to flow to the KOH treater, runaway temperatures are experienced which can cause hydrocarbons charged to vaporize and "blow up" the KOH treater with danger then of fires, etc. The present invention is directed to an improved system of controlling the flow of hydrocarbon streams containing HF to a KOH treater in order to prevent runaway temperatures and subsequent explosions.

Accordingly, an object of this invention is to provide an improved method and control system for the removal of HF from hydrocarbon streams.

A further object of this invention is to provide a temperature-sensitive control system for regulating the flow of hydrocarbon streams containing HF to a treater in a practical and economical manner.

A further object of this invention is to provide a sensitive and rapid response control system and method for the purification of hydrocarbon streams.

Other objects, aspects, and the several advantages of the invention will be apparent to those skilled in the art upon a study of this disclosure, the drawing, and appended claims.

In accordance with the invention, a method and a control system are provided for manipulating the flow of hydrocarbon containing HF to a KOH treater whereby the flow of hydrocarbon is regulated responsive to temperature changes in the separation system in a manner such that the temperature in the KOH treater does not exceed a preselected maximum allowable value.

In accordance with one embodiment, a small stream of hydrocarbon containing HF is passed through a small test bed of solid KOH located upstream of the main KOH treater; the flow of hydrocarbon containing HF to the main KOH treater is manipulated in response to a preselected maximum allowable temperature in the small test bed of solid KOH whereby a by-pass valve is opened and the main KOH charge line is closed when the temperature in the test bed of KOH reaches a preselected maximum value.

In accordance with another embodiment, a stripped stream of liquid propane removed from the upper portion of an alkylation HF stripper is passed through a small test bed of solid KOH upstream of the main KOH treater and when excess HF is present in the stripped stream the temperature in the test bed rises rapidly and in response to changes in the temperature in the test bed the flow of propane is manipulated whereby the propane is passed through a bypass line rather than be introduced into the main KOH treater in order to prevent runaway temperatures and explosions within the treater.

A better understanding of the invention will be obtained upon reference to the accompanying drawing, which is a schematic flow diagram of an alkylation process utilizing one embodiment of the invention.

Referring to the drawing, an alkylation system is illustrated comprising a reactor or contact zone 10 having inlet conduits 11 for olefin such as propylene and/or butylenes, 12 for isoparaffin such as isobutane, and 13 for rerun and makeup hydrogen fluoride (HF) catalyst. Effluent from contact zone 10 is removed via conduit 14 and passed to phase separator or settler 15 wherein the HF phase settles and is removed for recycle via conduit 16 to contact zone 10, with a portion being passed to a rerun system (not shown) for removal of impurities.

The hydrocarbon phase is removed from separation zone 15 by way of line 17 and passed to fractionation zone 18, which can be a plurality of distillation columns, wherein HF is removed by line 19; alkylate is removed by line 20; normal butane (vapor) is removed by line 21; and isobutane is removed by way of line 22 and recycled (not shown) to contact zone 10.

Propane is often present in the propylene feed, with fresh isobutane feed, and some propane is produced in the process. In order to prevent a buildup of propane in the system, a portion of the stream (sufficient to prevent propane buildup in recycle isobutane 22) is passed from conduit 17 by way of line 23 to depropanizer 24. Isobutane and higher boiling bottoms are passed by way of line 25 to conduit 17 and then to fractionator 18. Overhead product comprising propane, HF, and alkyl fluorides, when present, is passed by way of line 26 and condenser 27 to phase separator 28. Liquid HF accumulates in sump or leg 29 and is withdrawn by way of line 30. Hydrocarbon liquid, principally propane, containing dissolved HF and alkyl fluoride, e.g., isopropyl fluoride, when present, is withdrawn by way of line 31. A portion of the condensate in 28 is passed by way of line 32 as reflux to depropanizer 24.

The yield portion of the hydrocarbon liquid removed from settler 28 by line 31 is passed by way of line 33 to HF stripper 34 for removal of HF. Overhead product comprising HF and propane passes via conduit 35 and condenser 27 back to phase separator or accumulator 28. Bottoms product comprising propane and a small or trace amount of HF and, if not previously removed, containing alkyl fluorides (in which case there is a treatment thereof with such as bauxite or alumina upstream, not shown, of the KOH treater), is passed by way of conduits 36 and 37 to contact vessel 38 containing a bed of solid KOH. Propane of very substantially reduced fluoride content is removed as product by way of line 39. A slurry of water and KOH-HF reaction products (slough) is removed from KOH treater 38 by way of line 40 for disposal of or recovery of KOH. The propane product stream removed overhead from treater 38 by way of line 39 is substantially dry and free of fluorides.

The rate of withdrawal of bottoms product (which has been heated indirectly with steam) removed from the lower portion of stripper 34 by way of line 36 is controlled responsive to the liquid level in the lower portion of stripper 34. Liquid level controller 41 manipulates the position of valve 42 in accordance with the desired level of liquid in the bottom of stripper 34. The temperature of the bottoms stream removed from stripper 34 in line 36 is usually somewhat higher than desired for contact with KOH in treater 38, and, accordingly, is cooled in heat exchanger 43 to a temperature of about 100° F. (37.8° C.). The flow of heat exchange fluid through heat exchanger 43 is controlled by temperature controller 44 which regulates the position of valve 45 responsive to the temperature sensed in line 36 downstream of heat exchanger 43.

The partially cooled liquid hydrocarbon stream 36 is in part passed through a small test bed of KOH in vessel 46, and the remainder which is substantially a major portion of the liquid hydrocarbon stream is passed around the test bed 46 by way of line 47 and valved line 48 for introduction into KOH treater 38 by way of line 37. The temperature in test bed 46 is sensed by temperature controller 49 which is operatively connected to valve 50 and valve 51. Temperature controller 49 is set at a maximum allowable temperature for KOH bed 46 which temperature should not be exceeded to avoid runaway bed temperatures and possible explosions in either the test bed 46 or KOH treater 38. If the temperature in bed 46 reaches or exceeds the set temperature for temperature controller 49, temperature controller 49 will then actuate valves 50 and 51. Valve 50 is normally open and valve 51 is normally closed. However, during upset of the unit when excess HF is present and the temperature in test bed 46 exceeds the maximum allowable temperature, temperature controller 49 is actuated and in turn regulates the flow of hydrocarbon in line 47 by closing valve 50 and opening valve 51. The stream being by-passed can be sent through either line 52 and valved line 53 and line 49, or passed through valved line 54 for return to settler 15.

In actual operation, the liquid hydrocarbon stream containing residual HF is normally charged to the KOH treater 38 by way of line 37 at a temperature of about 100° F. (37.8° C.), and the stream contains a small amount of HF insufficient to cause significant increases of the temperature in KOH test bed 46. There is a slight warming in KOH test bed 46 when the normally small amount of HF, say, 10 to 50 ppm, is present in the charge introduced by line 36. When upset occurs with excess HF, as slugs of free HF, or, e.g., at least about several hundred ppm, flowing in or with the liquid feed to test bed 46 and treater 38, the KOH bed 46 temperature starts to increase rapidly. Temperature control means 49 which senses the temperature in KOH bed 46 is set for about 120°–130° F. (49°–54° C.). Thus, when 130° F. (54° C.) is reached, valve 50 which is normally open is closed and valve 51 which is normally closed is opened to allow the high HF-containing stream to be by-passed around treater 38 by way of lines 47, 52, and 53 or 54. If desired, an alarm can be sounded, say, at 120°–125° F. (49°–51.78° C.), and valves 50 and 51 can be manipulated as above between 125°–130° F. (51.78°–54° C.). These valves 50 and 51 are opposite acting; that is, one opens as the other closes. The valves in conduits 53 and 54 can be hand-operated with, normally, the valve in 53 being open and the valve in 54 being closed. During upset, the valve in 54 can be opened and the valve in 53 closed, or both valves in 53 and in 54 can be open.

The liquid propane (at about its bubble point) removed from the bottom of stripper 34 is at about 140° F. (60° C.) and a pressure of 285 psig (1,970 kPa gauge). The pressure in KOH treater 38 is a few pounds lower than in stripper 34, but at 100° F. (37.8° C.) inlet temperature the propane is below its bubble point. In order to prevent vaporization of propane in the KOH unit, the maximum temperature (to stop "flashing of liquid to vapor" and resulting disaster) is set at about 125°–130° F. (51.78°–54° C.) on temperature control means 49 so that only liquid will be in treater 38.

Stripper 34 is operated under conditions sufficient to take overhead most of the HF present in the feed together with some propane and as bottoms a propane stream substantially freed of HF. Stripper 34 can be heated indirectly by steam or other heating medium in a lower portion of the stripper, preferably by indirect heat exchange. In actual operation, for the stripping of HF from a propane stream, the temperature in the upper portion of stripper 34 is ordinarily in the range of about 105° F. to about 140° F. (40°–60° C.), and the bottom temperature is ordinarily about 120° F. to about 155° F. (49°–68° C.). The pressure existing in stripper 34 is ordinarily about 250 psig (1,725 kPa g.) to about 350 psig (2,415 kPa g.).

The fractionation system disclosed in the drawing uses a separate main column 18, along with the depropanizer 34-HF stripper 38 columns. Other conventional fractionation can be used upstream of the HF stripper, e.g., for example, as disclosed in U.S. Pat. No. 3,211,802, issued Oct. 12, 1965, to Dixon et al.

I claim:

1. In a process for removing HF acid from a hydrocarbon stream containing same by contacting with solid KOH in a treating zone, the steps of preventing excessive temperature increases above a preselected maximum allowable temperature and subsequent explosion in said treating zone when unexpected excess HF is present in said stream charged to said treating zone comprising:

passing a portion of said hydrocarbon stream through a small test bed of KOH, measuring the temperature in said test bed and producing a signal representative thereof, and controlling the flow of the remainder of said hydrocarbon stream in response to said signal by allowing the flow to pass to said treating zone when the measured temperature is below said preselected maximum allowable temperature, and stopping said flow of said hydrocarbon stream to said treating zone when excess HF is present in said hydrocarbon stream and the measured temperature of said test bed reaches and/or exceeds said preselected maximum allowable temperature, thereby diverting said hydrocarbon stream from being introduced into said treating zone.

2. A process according to claim 1 wherein said treating zone is provided with a by-pass loop around said treating zone and the flow of said hydrocarbon stream to said zone is diverted to said by-pass loop when the flow of said stream charged to said zone is stopped as the measured temperature reaches or exceeds said preselected maximum allowable temperature value.

3. A process according to claim 1 wherein said hydrocarbon stream comprises propane and is obtained from an HF stripping zone in an HF alkylation process and said preselected maximum allowable temperature is about 120°–130° F., the bubble point range for propane.

4. In a process for removing HF acid from a hydrocarbon stream containing same by stripping HF from said stream in a stripping zone and contacting the stripped hydrocarbon stream containing residual amounts of HF with solid KOH in a treating zone, the steps of preventing excessive temperature increases above a preselected maximum allowable temperature and subsequent possible explosion in said treating zone when unexpected excess HF is present in said stream charged to said treating unit comprising:

passing a portion of said hydrocarbon stream through a small test bed of KOH, measuring the temperature in said test bed and producing a signal representative thereof, and controlling the flow of the remainder of said hydrocarbon stream in response to said signal by terminating the flow of said hydrocarbon stream to said treating zone when excess HF is present in said hydrocarbon stream and the temperature of said test bed reaches and/or exceeds said preselected maximum allowable temperature and diverting said hydrocarbon stream from being introduced into said treating zone.

5. A process according to claim 4 comprising the additional steps of:

controlling the rate of removal of said hydrocarbon stream from said stripping zone responsive to the liquid level in a lower portion of said stripping zone, and cooling said hydrocarbon stream removed from said stripping zone and maintaining said stream under sufficient pressure to provide liquid phase conditions on introduction into said treating zone.

6. A process according to claim 4 wherein said hydrocarbon stream comprises propane and is cooled to about 100° F. prior to introduction into said treating zone and said preset maximum allowable temperature in said test bed is in the range of about 120°–130° F.

7. In a process for removing HF acid from a liquid hydrocarbon stream containing same by contacting with solid KOH in a treating zone, the steps of preventing excessive temperature increase above a preselected maximum allowable temperature, where at or above said maximum allowable temperature said liquid hydrocarbon would vaporize and result in an explosion and fire when an unexpected excess HF is present in said stream charged to said treating zone, said excessive temperature arising from the heat generated by the reaction between said HF and said solid KOH, said heat being absorbed by said hydrocarbon, comprising:

passing a portion of said hydrocarbon stream through a small test bed of KOH, measuring the temperature in said test bed and producing a signal representative thereof, and passing the remainder of said hydrocarbon stream to said treating zone, and terminating the flow of said remainder of said hydrocarbon stream to said treating zone when the temperature in said test bed reaches and/or exceeds said preselected maximum allowable temperature and diverting said remainder of said hydrocarbon stream from being introduced into said treating zone.

* * * * *